United States Patent [19]

Gyure et al.

[11] Patent Number: 5,034,389

[45] Date of Patent: Jul. 23, 1991

[54] RIBOFLAVIN COMPOSITION AND METHOD FOR PRODUCTION

[75] Inventors: Dale C. Gyure, Westminster; Daniel G. Dueppen, Fort Collins; Girish M. Patel, Lakewood, all of Colo.

[73] Assignee: Coors BioTech, Inc., Westminster, Colo.

[21] Appl. No.: 387,023

[22] Filed: Jul. 28, 1989

[51] Int. Cl.$^5$ .................. A61K 31/525; A61K 39/02; A61K 37/00
[52] U.S. Cl. ..................... 514/251; 424/92; 424/93
[58] Field of Search ............. 514/251, 904; 424/92, 424/93

[56] References Cited

U.S. PATENT DOCUMENTS

| | | | |
|---|---|---|---|
| 4,115,593 | 9/1978 | Henry | 426/53 |
| 4,374,135 | 2/1983 | Johnson | 514/218 |
| 4,397,927 | 8/1983 | Brog | 426/583 |

OTHER PUBLICATIONS

Zernov, V. S. Vitamin Enzyme Premixes for Fattening Pigs, Chem. Abs. 104:206047v (1985).
Tarasov V. N. et al., Premix From Products of Microbiological Synthesis in the Rations of Pigs Being Fattened, Chem. Abs. 85:31863t (1974).

*Primary Examiner*—Glennon H. Hollrah
*Assistant Examiner*—Gary E. Hollinden
*Attorney, Agent, or Firm*—Sheridan, Ross & McIntosh

[57] ABSTRACT

The invention involves a riboflavin composition comprising about 70% to about 90% by weight riboflavin and about 10% to about 30% by weight of a bulking agent selected from the group consisting of yeast, mold, fungi, bacteria and a mixture thereof, and having a bulk density greater than a riboflavin product having a purity of at least about 90% by weight. The riboflavin composition has improved flowability and reduced electrostatic charge relative to riboflavin products having a purity of at least about 90% by weight. The invention also involves a method for producing the riboflavin composition. The method comprises the steps of mixing riboflavin having a purity of at least about 90% by weight, a volatile, non-toxic liquid, and the bulking agent to produce a blend, and drying the blend.

15 Claims, No Drawings

RIBOFLAVIN COMPOSITION AND METHOD FOR PRODUCTION

FIELD OF THE INVENTION

The present invention relates to a riboflavin nutritional composition and a process for producing the same.

BACKGROUND OF THE INVENTION

Riboflavin, also known as vitamin $B_2$, vitamin G and lactoflavin, has physiological significance in the metabolism of protein, fat and nucleic acids. Because it is considered to be an essential B vitamin, riboflavin is added to poultry and livestock feeds to supplement naturally occurring levels. Total worldwide demand for riboflavin supplements is approximately 1.4 million kilograms.

Finished animal feeds are commonly produced through the mixing of concentrated premixes with the bulk of the feed. Premixes are a blend of the pure vitamin or nutrient with a suitable carrier. Mixing the premix with the bulk of the feed assures homogeneity or even distribution of the vitamin in the finished feedstock. If pure vitamin rather than a premix is added directly to the bulk of the feed, there is a greater likelihood of uneven distribution. Further, if the pure vitamin retains electrostatic charge, or has poor flowability or dispersability and/or is hygroscopic, its addition to bulk feed is even more likely to result in uneven distribution. For these reasons, the concentrated vitamin is not normally added directly to the bulk feed.

Products having a riboflavin concentration above 90% by weight typically have a low bulk density, develop electrostatic charge, have a smaller particle size and poor flowability and are hygroscopic. The tendency of particles to develop or retain electrostatic charge can cause adherence of the particles to the surfaces of weighing, transportation, mixing and storage devices. Electrostatic charge tends to increase with smaller particle size. It has been reported that the electrostatic charge of high purity riboflavin is due to the threadlike riboflavin crystals which tend to have polar ends. Hygroscopicity refers to the tendency of a substance to absorb moisture from the environment. Because of its hygroscopic nature, high purity riboflavin must be stored in a low-moisture environment. Flowability refers to the ease with which a substance flows in a smooth and uninterrupted fashion. Flowability generally increases with bulk density and is adversely affected by electrostatic charge and hygroscopicity.

To produce homogeneous distribution of a vitamin in a finished feedstock, feed manufacturers seek premixes having the following properties: vitamin stability, good flowability, minimal electrostatic effects, and minimal hygroscopicity. To conserve shipping costs which are based on both volume and weight and to minimize storage cost and facilitate handling, feed manufacturers seek premixes having a smaller volume made possible by high potency and high bulk density.

Efforts have been made in the past to produce a riboflavin product having minimal electrostatic charge, high potency, high bulk density, improved flowability and minimal hygroscopicity. In Cannalonga et al., U.S. Pat. No. 3,959,472 (1976), oyster shell flour and maltrin are added to produce a riboflavin product reported to be free-flowing, non-dusting and static free. The product is described as comprising 45–65% riboflavin with a bulk density of 35–36 pounds per cubic foot (lbs/ft$^3$). The composition is produced by spray drying an emulsion to produce a final product having by weight 45–65% riboflavin; 15–25% oyster shell flour; 15–35% maltrin; and 1–5% silicic acid.

Other riboflavin products known to exist in the market contain other carriers which may serve to reduce electrostatic charge, increase bulk density and improve flowability. "MICROVIT RIBO" TM feed supplement produced by Rhone Poulenc contains soy flour and oil and dry fermentation solubles. "ROVIMIX B2 80 SD" TM feed supplement manufactured by Hoffmann LaRoche contains 20% by weight skim milk.

As described above, riboflavin products having a purity greater than 90% by weight typically are hygroscopic and have electrostatic properties that are detrimental to flowability. Products having lower riboflavin concentrations have lower potencies which in turn can mean greater shipping and storage costs. Thus there is a need for a riboflavin containing material having a higher bulk density and a greater potency to minimize volume and shipping costs while having minimal electrostatic charge and hygrocopicity to enhance flowability. It would be particularly advantageous if the above physical characteristics could be produced by the addition to substantially pure riboflavin of a carrier having a low cost.

It has now been found that the composition of the present invention fulfills these needs by using a carrier which is also inexpensive and readily available.

SUMMARY OF THE INVENTION

The instant invention comprises a riboflavin composition comprising about 70% to about 90% by weight riboflavin and about 10% to about 30% by weight of a bulking agent. The riboflavin composition has increased bulk density, improved flowability and reduced electrostatic charge relative to riboflavin products having a purity of at least about 90% by weight. In another embodiment, the instant invention involves a method for producing the riboflavin composition. The method comprises the steps of mixing riboflavin having a purity of at least about 90% by weight, a volatile, nontoxic liquid, and the bulking agent to produce a blend, and drying the blend.

DETAILED DESCRIPTION OF THE INVENTION

The instant invention comprises a riboflavin composition having a high bulk density and potency, good flowability, and minimal electrostatic charge, and a method for producing the same. The riboflavin composition comprises between about 70% and about 90% by weight of riboflavin, and between about 10% and about 30% by weight of yeast, mold, bacteria, fungi or a mixture thereof, which act as bulking agents and impart such desirable properties as high bulk density, good flowability, and minimal electrostatic charge to the riboflavin composition.

The method of the present invention comprises the following steps: mixing an amount of a riboflavin product having a purity of about 96% by weight with an amount of a volatile, non-toxic liquid, and an amount of a dried yeast, mold, bacteria, or fungi or mixture thereof, sufficient to produce a blend that, when dried, has a riboflavin concentration between about 70% and about 90% by weight, and has a greater bulk density, an improved flowability and a reduced electrostatic charge relative to a riboflavin product having a purity of at least about 90% by weight.

As discussed hereinabove, the riboflavin composition is comprised primarily of riboflavin and a bulking agent selected from the group consisting of yeast, mold, fungi, bacteria or a mixture thereof, in a weight ratio of between about 7:3 to about 9:1. The composition can also comprise between about 2% and about 8% by weight water or other volatile, non-toxic liquid, between about 0% and about 2% by weight ash, and between about 0% and about 2% by weight fermentation solubles. "Fermentation solubles" as used herein means cell lysis products and media nutrients. The composition can further comprise additional vitamins or nutrients such as amino acids. The riboflavin composition has a greater bulk density, reduced electrostatic charge and improved flowability relative to riboflavin having a purity of at least about 90% by weight.

As used herein, "reduced electrostatic charge" is determined relative to riboflavin of at least about 90% by weight purity. A convenient method of making such a comparison by the skilled artisan is to observe whether the subject composition has reduced adherence to handling equipment relative to the adherence observed with riboflavin having a purity of at least about 90% by weight. A composition has improved flowability relative to riboflavin of at least about 90% by weight purity if the flowability of the composition, as measured by ASTM method B213-83 modified as provided in Example 2 hereinbelow, is greater than the at least 90% riboflavin material. A composition has improved bulk density relative to riboflavin of at least about 90% by weight purity if the bulk density, or weight per unit volume, is greater than that of a riboflavin product having a purity of at least about 90% by weight. Specific bulk densities that can be obtained in certain embodiments are described hereinbelow in Examples 2 through 4.

The riboflavin composition of the present invention can be used in animal feed or human nutritional compositions. Additionally, because of the yellow color imparted to the composition by riboflavin, the riboflavin composition can be used as a coloring agent.

The source of riboflavin for the composition of the present invention is a riboflavin product having a riboflavin content of at least about 90% by weight, and preferably at least about 96% by weight. Riboflavin products having riboflavin contents greater than about 90% by weight typically have low bulk densities, retain electrostatic charge and have poor flowabilities. The addition of a bulking agent to riboflavin having a riboflavin content of at least about 90% by weight can improve flowability and reduce electrostatic charge. Although a riboflavin product having a riboflavin content of less than 96% by weight can be used as a feed material for the method of the present invention, riboflavin products having a purity of at least 96% by weight are those most likely to benefit from the addition of a bulking agent such as yeast, mold, fungi, bacteria or a mixture thereof. The term riboflavin product "purity" is used herein to refer to the weight percentage of riboflavin in a riboflavin product.

The riboflavin feed material of at least about 90% by weight purity, i.e., contains at least about 90 weight percent riboflavin, can, in its weight balance, contain water, ash and/or fermentation solubles.

The riboflavin feed material can be any of the A, B or C crystal types. The riboflavin crystal type is not believed to have any effect on the bulk density or other desired qualities of the final riboflavin composition of the instant invention.

The yeast, mold, bacteria or fungi used as the bulking agent component of the subject composition can be any such microorganism that is non-toxic and non-pathogenic to humans and animals, and is dried and inactivated (non-fermentative). Yeasts that can be used in the instant method include, but are not limited to, *S. Uvarum* (syn. *S. carlsbergensis*), *S. lactis, Kluyveromyces fragilis* (syn. *Saccharomyces fragilis*), *Candida utilis* (torula yeast), and *Candida guillienmondis*. A preferred yeast is *Saccharomyces cerevisiae* or brewer's yeast. Molds that can be used for the instant process include, but are not limited to, *Fusarium graminearum, Penicillium cyclopium*, and *Trichoderma harzianum*. Fungi include, without limitation, *Paecilomyces varioti*, and *Chaetomium cellulolyticum*. Bacteria include, but are not limited to, *Methylophilus methylotrophus*.

As discussed hereinabove, the method of the present invention uses a riboflavin feed material having a riboflavin content of at least about 96% by weight. The riboflavin feed material is mixed with a preselected quantity of liquid to produce a riboflavin slurry. The liquid is volatile and must be non-toxic to animals and humans in the quantities present in the final riboflavin composition produced by the instant method. For example, the liquid can be water or ethanol.

The slurry is then blended with a quantity of yeast, mold, fungi or bacteria or a mixture thereof, to produce a blend. The yeast, mold, fungi or bacteria can be any of those identified hereinabove.

The amount of liquid added to the riboflavin and bulking agent to produce the blend is that amount which, for a particular drying process, results in a riboflavin composition having a bulk density greater than the bulk density of a riboflavin product having a purity of at least about 90% by weight. While the quantity of liquid added to produce the blend determines the upper limit on the amount of residual moisture in the product, it is the blending and drying process that ultimately determines the bulk density and residual moisture of the product, respectively. For example, when spray drying is used to dry the wet blend, it has been found that mixing the liquid with the 96% by weight riboflavin and the bulking agent results in a spray-dried riboflavin composition that has a greater bulk density than a composition produced by dry mixing the 96% by weight riboflavin with the bulking agent. For example, it is preferred that the conditions of a particular drying process, such as temperature and duration, be selected so as to result in a residual moisture in the riboflavin composition product that aids in imparting a bulk density that is greater than the bulk density of a riboflavin product having at least about 90% by weight purity. Up to 8% by weight of liquid can be retained in the dried riboflavin composition to enhance bulk density and minimize electrostatic charge.

The bulk density is known, in the case of spray drying, to be dependent in part on the solids concentration of the blend. It has been observed that the greater the solids concentration of the blend, the greater the bulk density of the riboflavin composition product. Thus, the amount of liquid in the riboflavin/bulking agent/liquid blend is that quantity that is sufficiently small to produce a solids concentration in the blend that results in a riboflavin composition product having a bulk density greater than that of a riboflavin product having at least about 90% by wight purity. However, the amount of liquid added to the 96% by weight riboflavin and the bulking agent should also be a quantity sufficient to assure homogenous distribution of the liquid in the blend. The exact quantity of liquid to be added to the riboflavin and bulking agent can be readily determined by one skilled in the art.

Preferably, the solids concentration of the riboflavin/liquid/bulking agent blend is sufficiently high to minimize the amount of liquid to be evaporated, thereby minimizing the time and operation expense of the drying process. However, the economic considerations for having a high solids concentration in the blend must be weighed against the need for sufficient liquid to produce the desired solids concentration and the need for uniform mixing of the liquid in the blend. The solids concentration in the riboflavin/liquid/bulking agent blend is therefore typically between about 5% and 25% by weight, and preferably between about 15% and about 20% by weight to allow for an adequate solids concentration and even liquid distribution in the blend while minimizing dryer operating cost.

For example, if the liquid used is water, the bulking agent is dried brewer's yeast (*Saccharomyces cerevisiae*), and the drying process is spray drying, the desired solids concentration of the riboflavin/yeast/water wet blend has been determined to be about 150 g/l. That is, the solids concentration of about 150 g/l has been found to result in a spray-dried riboflavin composition that has a bulk density of between about 5 and about 8 kg/ft$^3$ and has improved flowability and reduced electrostatic charge relative to riboflavin of about 96% purity. To produce a riboflavin/yeast/water blend having a solids concentration of about 150 g/l, the amount of water that is added to the 96% by weight riboflavin feed material to produce the slurry is a volume sufficient to produce a riboflavin concentration of about 120 g/l; an amount of yeast is then added to raise the solids concentration to the desired 150 g/l. This combination results in a riboflavin composition having a riboflavin concentration of between about 70% and about 90% by weight and a yeast concentration of between about 10% and about 30% by weight, with a bulk density of between about 5 and about 8 kg/ft$^3$.

The solids concentration of about 150 g/l for the riboflavin/yeast/water blend has an amount of water that is sufficient, when spray-dried under conditions described in Example 1 hereinbelow, to produce a riboflavin composition having a bulk density of between about 5 and about 8 kg/ft$^3$. However, a decrease in the water content in the blend resulting in an increase of the solids concentration above about 150 g/l can result in an increase in the bulk density of the riboflavin composition product.

Drying of the wet blend to produce a riboflavin composition having the desired physical properties can be accomplished by spray drying alone, or by other drying methods such as tray drying, vacuum oven drying, fluid bed drying or combinations thereof, followed by grinding with mechanical grinding means such as media mills, roll mills, colloid mills, fin-grinding hammer mills and/or jet mills, to reduce the composition particles to a size that disperses efficiently and yet has minimal electrostatic charge and improved flowability. It has been found that a particle size of less than about 40 microns is effective to give adequate dispersion while minimizing electrostatic charge.

As discussed hereinabove, the bulk density of the spray-dried riboflavin/ brewer's yeast/water blend has been found to be dependent upon the operating conditions of the spray dryer. The residual moisture content of the riboflavin composition product must be sufficient to produce the desired bulk density, but not so great as to cause the composition to become sticky or clumpy and impair the composition's flowability. If the spray-dryer inlet and outlet temperatures exceed the temperatures described in Example 1 hereinbelow, the composition can be scorched. Scorching can result in decomposition of the riboflavin, impaired bioactivity and decreased flowability. If the inlet or outlet temperatures drop below those specified in Example 1, the blend is inadequately dried resulting in a sticky or wet product with poor flowability.

The following examples are given for illustrative purposes only and are not meant to be a limitation of the subject invention.

Examples

EXAMPLE 1

A preferred method for preparation of the riboflavin composition of the present invention follows: sufficient water was added to a riboflavin feed material having a purity of about 96% to create a riboflavin slurry having a riboflavin concentration of about 120 g/l; the slurry was then wet blended with an amount of dried brewer's yeast sufficient to produce a blend having a solids concentration of about 150 g/l; the blend was then spray-dried in a spray dryer having an inlet temperature of 200°-220° C. and an outlet temperature of 80°-85° C. The spray dryer can be a spinning disk atomizer or any other nozzle type. It is especially preferred that the spray dryer outlet temperature be about 80° to about 82° C. It has been found that a composition spray-dried in this outlet temperature range has a slightly greater bulk density than a composition spray-dried in a spray-dryer having an outlet temperature greater than 82° C. and up to about 105° C.

The above method was used for the preparation of all of the following runs unless otherwise noted.

EXAMPLE 2

Runs 1 through 4 illustrate that flowability, bulk density and particle size of spray-dried riboflavin compositions are improved by the addition of yeast.

For runs 1 and 3, the method of Example 1 was not followed; instead they were prepared by spray drying a slurry of 96% by weight riboflavin and water with no added carrier in a spinning disk atomizer spray dryer. Runs 1 and 3 were spray dried in a spray-dryer having an inlet temperature between about 200° C. and about 220° C. and the outlet temperature of about 105° C. The riboflavin feed material for runs 1 and 3 were from different riboflavin production lots, with each lot having a purity of about 96% by weight. Runs 1 and 2 utilized riboflavin from the same riboflavin production lot. Runs 3 and 4 utilized riboflavin from a second riboflavin production lot.

Runs 2 and 4 were prepared by the method of Example 1, with the exception that the spray-dryer outlet temperature was about 105° C. The spray dryer was a spinning disk atomizer.

For the method of Example 1 using a spinning disk atomizer having an outlet temperature of between about 80° and about 85° C., the frequently obtained and preferred range of bulk densities is between about 5 and about 8 kg/ft³. As illustrated by runs 2 and 4, which were dried at an outlet temperature of about 105° C., the bulk densities remained within this preferred range, but were at the lower end of the range. This reduced bulk density could be due to reduced residual moisture in runs 2 and 4 due to the increased outlet temperature of 105° C.

Flowability was measured by ASTM method B213-83 modified in the following way: a Syntron Magnetic Vibrator V-4-AC manufactured by FMC Corp. was attached to the top of the vertical member of the ring stand and set at 25% power to permit the flow of test materials through the funnel. The results obtained follow:

| Run | Bulk Density (g/cc) | Flowability (g/sec) | Average Particle Size (microns) |
|---|---|---|---|
| 1. 96% $B_2$ | 0.053–0.067 | 0.026 | 0.80 |
| 2. 78–80% $B_2$; 20% yeast | 0.179–0.198 | 0.480 | 1.68 |
| 3. 96% $B_2$ | 0.056 0.085 | 0.098 | 1.05 |
| 4. 78–80% $B_2$; 20% yeast | 0.180–0.233 | 0.403 | 2.20 |

EXAMPLE 3

Runs 5 through 10 illustrate the significance of spray dryer outlet temperature on the bulk density.

Runs 5 and 8 utilized riboflavin feed material from different riboflavin production lots. Runs 5 and 8 were prepared by spray drying a slurry of 96% by weight riboflavin and water with no added carrier in a spinning disk atomizer. Runs 5 and 8 were spray-dried at an inlet temperature of about 200° to about 220° C. and an outlet temperature of about 105° C. Runs 5, 6 and 7 each used riboflavin feed material from the same production lot. Runs 8, 9 and 10 each used riboflavin feed from a second riboflavin production lot.

Runs 6, 7, 9 and 10 were prepared by the method described in Example 1, with the exception that the outlet temperatures were as indicated in the table below. Runs 6, 7, 9 and 10 were spray-dried in a spinning disk atomizer.

Flowability for each run was measured by the method described for in Example 2.

A comparison of run 6 with run 7, and run 9 with run 10, illustrates that bulk density, flowability and average particle size generally increase with lower outlet temperatures. A comparison of run 6 with run 9 indicates that as the outlet temperature drops below the preferred range of 80°-85° C., the flowability, bulk density and average particle size decrease. A comparison of run 9 and run 10 indicates that as outlet temperature exceeds the preferred range of 80°-85° C., bulk density, flowability and particle size all decrease.

| Run | Outlet | Bulk Density (g/cc) | Flowability (g/sec) | Average Particle Size (microns) |
|---|---|---|---|---|
| 5. 96% $B_2$ | 105° C. | 0.065-0.095 | 0.024 | 0.95 |
| 6. 78–80% $B_2$; 20% yst | 70° C. | 0.161-0.183 | 0.066 | 2.65 |
| 7. 78–80% $B_2$; 20% yst | 105° C. | 0.124–0.161 | 0.055 | 1.75 |
| 8. 96% $B_2$* | 105° C. | | | |
| 9. 78–80 $B_2$; 20% yst | 80° C. | 0.220–0.234 | 0.073 | 3.6 |
| 10. 78–80% $B_2$; 20% yst | 105° C. | 0.204–0.217 | 0.071 | 2.9 |

* Data not obtained. Data expected to be similar to runs 1, 3 and 5, i.e., about 0.050–0.095 g/cc for bulk density; about 0.024–0.098 g/sec for flowability; and about 0.80–1.05 microns for the average particle size.

EXAMPLE 4

Runs 11 through 14, when compared to runs 2 and 4, illustrate there is no significant difference between a spray-dried, 80% riboflavin/20% nonfat milk product and a spray-dried, 80% riboflavin/20% dried brewer's yeast product in terms of flowability and bulk density. This conclusion is significant in light of the fact that dried brewer's yeast is a more economical feed material than nonfat milk.

Runs 11 and 13 were from different production lots, each lot having a riboflavin purity of about 96% by weight. Runs 11 and 13 were prepared by spray drying a slurry of 96% by weight riboflavin and water with no added carrier in a spinning disk atomizer spray dryer. For runs 11 and 13, the spray-dryer inlet temperature was about 200° to about 220° C. and the outlet temperature was about 105° C. Runs 11 and 12 used riboflavin feed from the same production lot. Runs 13 and 14 used riboflavin feed from a second production lot.

Runs 12 and 14 were prepared in the same manner described in Example 1, with the exceptions that non-fat milk was used in place of dried brewer's yeast and the spray dryer outlet temperature was 105° C. Runs 12 and 14 were spray-dried in a spinning disk atomizer.

The flowability was measured in the same manner described in Example 2. The data obtained was as follows:

| Run | Bulk Density (g/cc) | Flowability (g/sec) | Average Particle Size (microns) |
|---|---|---|---|
| 11. 96% $B_2$ | 0.053–0.067 | 0.026 | 0.8 |
| 12. 80% $B_2$; 20% milk | 0.163–0.203 | 0.280 | 2.2 |
| 13. 96% $B_2$ | 0.056–0.085 | 0.098 | 1.05 |
| 14. 80% B; 20% milk | 0.166–0.233 | 0.692 | 3.40 |

It will be understood that the above description of the present invention is susceptible to various modifications, changes and adaptations and the same are intended to be comprehended within the meaning and range of equivalents of the appended claims.

What is claimed is:

1. A riboflavin composition comprising between about 70% and about 90% by weight riboflavin and between about 10% and about 30% by weight of a bulking agent selected from the group consisting of yeast, mold, bacteria and fungi, said composition having a bulk density greater than about 5 kg/ft³.

2. The riboflavin composition of claim 1, wherein said riboflavin comprises between about 75% and about 80% by weight.

3. The riboflavin composition of claim 2, wherein said bulking agent is dried brewer's yeast.

4. A riboflavin composition having a riboflavin concentration between about 70% and about 90% by weight and a bulk density greater than about 5 kg/ft$^3$ by weight produced by the process comprising the steps of:
providing riboflavin having a riboflavin concentration of at least about 90% by weight;
mixing amounts of a non-toxic, volatile liquid, a bulking agent and said riboflavin sufficient to produce a blend, said bulking agent selected from the group consisting of yeast, mold, bacteria, fungi and mixtures thereof; and
drying said blend to produce said riboflavin composition.

5. The riboflavin composition of claim 4, wherein said step of providing riboflavin comprises providing riboflavin having a riboflavin concentration of at least about 96% by weight.

6. The riboflavin composition of claim 5, wherein
said step of mixing said non-toxic, volatile liquid, said bulking agent and said riboflavin comprises mixing an amount of water, yeast and said riboflavin sufficient to create a blend having a riboflavin concentration of about 120 g/l and a solids concentration of about 150 g/l; and
said step of drying comprises spray-drying said blend in a spray dryer having an inlet temperature of between about 200° C. and about 220° C. and an outlet temperature of between about 80° C. and about 85° C. to produce said riboflavin composition.

7. The riboflavin composition of claim 6, wherein said yeast is dried brewer's yeast.

8. The riboflavin composition of claim 6 wherein said step of spray drying comprises drying in a spray dryer having an outlet temperature of between about 80° C. and about 82° C.

9. A method for producing a riboflavin composition having a riboflavin concentration of between about 70% and about 90% by weight and a bulk density greater than about 5 kg/ft$^3$, said method comprising:
providing riboflavin having a riboflavin concentration of at least about 90% by weight;
mixing amounts of a volatile, non-toxic liquid, a bulking agent and said riboflavin sufficient to create a blend, said bulking agent selected from the group consisting of yeast, mold, bacteria, fungi and mixtures thereof; and
drying said blend to produce said riboflavin composition.

10. The method of claim 9, wherein said step of providing riboflavin comprises providing riboflavin having a riboflavin concentration of at least about 96% by weight.

11. The method of claim 10, wherein:
said step of mixing said non-toxic, volatile liquid, said bulking agent and said riboflavin comprises mixing amounts of water, yeast, and said riboflavin sufficient to create a blend having a riboflavin concentration of about 120 g/l and a solids concentration of about 150 g/l; and
said step of drying comprises spray-drying said blend in a spray dryer having an inlet temperature of between about 200° C. and about 220° C. and an outlet temperature of between about 80° C. and about 85° C. to produce said riboflavin composition.

12. The method of claim 11, wherein said yeast is dried brewer's yeast.

13. The method of claim 11, wherein said step of spray drying comprises drying in a spray dryer having an outlet temperature of between about 80° C. and about 82° C.

14. A riboflavin composition having a riboflavin concentration between about 70% and about 90% by weight and a bulk density greater than about 5 kg/ft$^3$, produced by the method comprising the steps of:
providing riboflavin having a riboflavin concentration of at least about 90% by weight;
mixing amounts of a non-toxic, volatile liquid, a bulking agent and said riboflavin sufficient to produce a blend, said bulking agent selected from the group consisting of yeast, mold, bacteria, fungi and mixtures thereof;
drying said blend to produce said riboflavin composition; and
milling said riboflavin composition to produce a riboflavin composition having a particle size less than about 40 microns and having improved flowability and reduced electrostatic charge relative to a riboflavin composition having a riboflavin concentration of at least about 90% by weight.

15. A method for producing a riboflavin composition having a riboflavin concentration between about 70% and about 90% by weight and a bulk density greater than about 5 kg/ft$^3$, said method comprising:
providing riboflavin having a riboflavin concentration of at least about 90% by weight;
mixing amounts of a non-toxic, volatile liquid, a bulking agent and said riboflavin sufficient to produce a blend, said bulking agent selected from the group consisting of yeast, mold, bacteria, fungi and mixtures thereof;
drying said blend to produce said riboflavin composition; and
milling said riboflavin composition to produce a riboflavin composition having a particle size less than about 40 microns and having improved flowability and reduced electrostatic charge relative to a riboflavin composition having a riboflavin concentration of at least about 90% by weight.

* * * * *